United States Patent [19]

Makino et al.

[11] Patent Number: 5,626,871
[45] Date of Patent: May 6, 1997

[54] PREPARATION FOR INTRATRACHEOBRONCHIAL ADMINISTRATION

[75] Inventors: Yuji Makino; Hideki Kobayashi; Yoshiki Suzuki, all of Hino, Japan

[73] Assignee: Teijin Limited, Osaka, Japan

[21] Appl. No.: 193,141

[22] PCT Filed: Jun. 11, 1993

[86] PCT No.: PCT/JP93/00785

§ 371 Date: Feb. 14, 1994

§ 102(e) Date: Feb. 14, 1994

[87] PCT Pub. No.: WO93/25193

PCT Pub. Date: Dec. 23, 1993

[30] Foreign Application Priority Data

Jun. 12, 1992 [JP] Japan ................................ 4-153538

[51] Int. Cl.$^6$ .................. A61K 9/48; A61K 9/72; A61K 9/14

[52] U.S. Cl. .................................... 424/451; 424/499
[58] Field of Search .......................... 424/451, 499

[56] References Cited

U.S. PATENT DOCUMENTS

| | | | |
|---|---|---|---|
| 3,634,582 | 1/1972 | Hartley et al. | 424/14 |
| 4,161,517 | 7/1979 | Bell | 424/14 |
| 4,294,829 | 10/1981 | Suzuki et al. | 424/241 |

FOREIGN PATENT DOCUMENTS

| | | |
|---|---|---|
| 59-34267 | 2/1984 | Japan . |
| 61-100519 | 5/1986 | Japan . |

*Primary Examiner*—Frederick Krass
*Attorney, Agent, or Firm*—Sughrue, Mion, Zinn, Macpeak & Seas

[57] ABSTRACT

A preparation for intratracheobronchial administration comprising a powder preparation for intratracheobronchial administration contained in a receptacle composed essentially of hydroxypropyl methyl cellulose.

13 Claims, No Drawings

PREPARATION FOR INTRATRACHEOBRONCHIAL ADMINISTRATION

TECHNICAL FIELD

The present invention relates to a preparation for intratracheobronchial administration. More specifically, the present invention relates to a preparation for intratracheobronchial administration, comprising a powder preparation for intratracheobronchial administration contained in a receptacle composed of at least one component selected from the group consisting of hydroxypropyl methyl cellulose, methyl cellulose, hydroxypropyl cellulose, starches, hydroxypropyl starches, and sodium alginate. Furthermore, specifically, the present invention is concerned with a preparation for intratracheobronchial administration, contained in a receptacle, in which a medicament in the powder preparation for intratracheobronchial administration is contained in the receptacle composed of at least one component of cellulose derivatives-analogues, that is, selected from the group consisting of hydroxypropyl methyl celluloses, methyl celluloses, hydroxypropyl celluloses, starches, hydroxypropyl starches, and sodium alginate, and the medicament is not easily adhered to the receptacle so that the amount of the intratracheobronchially delivered medicament is improved.

BACKGROUND ART

The airway extending from the nasal cavity, oral cavity to the pharynx, larynx, trachea, bronchia, bronchioles, and alveoli is a passageway for expiratory and inspiratory air.

In the airway, there occur many diseases such as nasal allergies, asthma, bronchitis, lung emphysema, and the like. The method for administering a medicament in the pharmacotherapy for these diseases may be classified into the whole body administration such as the use of orally administered medicaments and injections, and intratracheobronchial local administration such as the use of nebulas, inhalants, and the like.

Oral administration is an easy method, and the use of injections ensures the absorption of the injections into the body, and therefore, these administering methods have widely been employed. However, intratracheobronchial administration of a medicament is highly valuable in the light of convergence of the medicament into an acting site, reduction of adverse side effects due to the convergence, and fast-acting properties of the effect of the medicament.

Further, in addition to the local administration of a medicament for such diseases as mentioned above, which occur in the airway, there has recently been a trial of proceeding a medicament from alveoli to blood by utilization of the fact that the barrier between the alveoli and blood is dwarfish, and the intratracheobronchial administration has now attracted public attention as a systemic administration method for peptides, proteins or the like, which are metabolized in the gastrointestinal tract, liver or the like so as to be inactivated, when these are orally administered.

In addition, there have been attempts to locally administer a vaccine in the airway by utilizing the antigen recognizing function of the lymphatic system in the airway, so as to prevent and treat a disease. Therefore, it may be said that the importance of intratracheobronchial administration is very significant.

The preparations for intratracheobronchial administration to be used for the above intratracheobronchially administering method can be classified into the following two kinds, with respect to the properties of the particles of the preparations: (1) preparations, the droplets of which are deposited to the inside of the airway, and (2) preparations, the fine solid particles of which are deposited to the inside of the airway.

A preparation (1) is usually an aqueous solution containing a medicament, which is atomized by a nebulizer, and inhaled into the airway as minute droplets. Preparations (2) are further roughly classified into (i) aerosol preparations, in which the fine solid particles are contained in a pressure container in a state such that they are dispersed in a fluorohydrocarbon, and when they are discharged out of the vessel in the case of the use thereof, these particles move in the airway together with the fluorohydrocarbon, and after the fluorohydrocarbon has rapidly evaporated, they are finally deposited in the airway, as fine solid particles of the medicaments, and (ii) powder preparations in which a medicament is contained as fine solid particles in receptacle, and in the case of using any of them, the fine solid particles of the medicament are inhaled into the airway directly from the container or by use of an administration utensil, by injection or inhalation of breath, and deposited to the inside of the airway as fine solid particles of the medicament.

These preparations have already been put to practical use, regarding all the types thereof. The liquid preparations of (1) require a nebulizer or atomizer and are therefore, not convenient to carry. The fluorohydrocarbon aerosol preparations of (2)-(i) are simple to handle, and have been widely used, but there has arisen a trend of public opinion to restrict the use of these preparations, considering the problem of air pollution from fluorohydrocarbon gases. Under such circumstances, powder preparations for intratracheobronchial administration of (2)-(ii), which have remained comparatively backward in the development as compared with the other two kinds of preparations, have come to noticeably attract public attention.

In order to administer a powder preparation for intratracheobronchial administration, a receptacle for the powder preparation and an administering utensil are needed. In the following, the "receptacle" means a receptacle in which the powder preparation is directly contained, and the powder preparation is contained in the receptacle, after it has been prepared by mixing and stored until it is used. Therefore, the receptacle is ordinarily tightly sealed. In addition, the administering utensil in the present invention is generally a device for taking the powder preparation out of the above-mentioned receptacles containing the powder preparation in such a state as can be administered into the airway; it is, e.g., a device for maintaining the tightly sealed powder preparation at a proper position, and boring a hole in the receptacle so as to enable the powder preparation to proceed into the airway. The receptacle and administering utensil are usually separately produced, but they may be produced as an integrated product. For example, a part of a receptacle is removed when using the powder preparation, so as to produce a hole, whereby it becomes possible to cause the powder preparation contained in the receptacle to move into the respiratory tract from the receptacle.

The powder preparation, which has been made movable into the airway from the receptacle by use of an administering utensil or by performing some operations in an integrated product of a receptacle and administering utensil, is delivered into the airway by utilization of the inhalation of the breath of the user (patient) or of a gas from a pressurized gas cylinder or by some other device.

The receptacle and administering utensil for the powder preparation for intratracheobronchial administration are classified into the following two types according to the dose of the powder preparation in the receptacle: (i) a type in which the dose of the powder preparation to be delivered into the airway per one time has preliminarily been set apart and contained in each receptacle (unit dose type), and (ii) a type in which a multidose of the powder preparation is contained in the receptacle, and dose of the powder preparation is divided up by some means and sent into the airway every time the preparation is to be used (multidose type).

For the above two types of containing systems, there have been devised many administering utensils, and as specific examples thereof, there may be mentioned, e.g., as a unit dose type, the powder medicine-dispensing device disclosed in Japanese Examined Patent Publication (Kokoku) No. 63-6024, "Spinhaler" (Registered Trade Mark), "Rotahaler" (Registered Trade Mark), "Diskbaler" (Registered Trade Mark) or the like described in "Respiratory Drug Delivery" edited by P. R. Byron, published by CRC Press, 1990, p.169, and as a multidose type, "Turbohaler" (Registered Trade Mark) described on p.169 of the same publication, and the like.

The shapes of receptacles for containing a powder preparation vary in many ways depending on the above containing systems or the structure of the administering utensils. As the unit dose type receptacles, there have hitherto been known, e.g., hard medical capsules which have been widely used for oral preparations; disk-shaped molded products which can be charged in a "Diskhaler" (Registered Trade Mark); and disposable receptacles as proposed in WO 89/01348 Specification. In addition, as multidose type receptacles, there have been known the receptacles of such shapes as can be changed in conformity with the structure of an administering utensil and a predetermined amount of the content of the receptacle can be moved from the administering utensil to the airway. In the present invention, there may be used any of the receptacles of these shapes. In addition, a receptacle may constitute a part of an administering utensil. For example, a receptacle may be cylindrical and, simultaneously, have a structure such that the receptacles can be removed from its cap and fixed to an administering utensil by driving a screw.

On the other hand, with respect to the material of a receptacle containing the powder preparation, even if the present powder preparation is in the form of an inhalant that is administered into the airway of the human body, the receptacles are in direct contact with the powder preparation. Accordingly, as the materials which have specifically been known as those of the receptacles containing powder preparations, in consideration of safety and the like, there may be mentioned, as unit dose type ones, hard gelatin medical capsules which have widely been used for oral preparations; aluminium to be molded into a disk-shaped product (see e.g.p.169 of the above-mentioned publication published by R. Byron); or plastics, mainly polyolefinic ones such as polyethylene, polypropylene, and polystyrene, which have been proposed for disposable receptacles. In addition, as the materials of multidose type receptacles, there may be mentioned plastics, mainly polyolefinic ones such as polyethylene, polypropylene, and polystyrene; aluminium; glass; and the like.

As the powder preparations to be contained in the receptacles made of various materials, there have been known powder of a medicament itself alone, which is administered into the airway and deposited thereto, whereupon the effect of the medicine is exhibited at an affected part or the preparation is transferred to the whole body from the affected part and the effect of the medicines exhibited in the whole body, or mixtures thereof with an appropriate diluent, e.g. lactose, mannitol, crystallite cellulose and the like.

With respect to such a powder preparation for intratracheobronchial administration, since it is necessary to reach a target region with good efficiency and broaden the deposited area at the reached region, the particle diameter of the powder should be reduced. The interrelation between the particle diameter of the particles and the region attained by the preparation has been examined by many investigators, and though their reported values are not always consistent with other, it is said that, for example, particles with a particle diameter larger than 10 μm, but up to about 500 μm, are deposited mainly in the oral cavity and nasal cavity, particles with a particle diameter above 2 μm and not more than 10 μm are deposited mainly in the trachea, bronchi, and bronchioles and those having a particle diameter ranging from 0.5 to 2 μm are deposited mainly in the alveoli. (see "The Newest Biopharmacology" edited by Awazu and Koizumi, published by Nankodo Publishers, 1991, p.67). The above-mentioned particle size is applied to a medicament particle alone in the powder preparation and a particle comprising a medicament, but not to an additive particle.

According to the technique regarding the above powder preparation for intratracheobronchial administration, the present inventors have continued their studies concerning the administration of powder medicaments into the nasal cavity, bronchi, alveoli or the like, and been confronted with significant technical problem on the basis of the fact that the above-mentioned powder preparation is a powder of fine particles.

That is, it has been found that, while a powder preparation is contained in the above-mentioned various receptacles and stored, or while it is charged in administering utensils, the powder preparation comes in contact with the receptacle owing to vibration, so that the fine particles of a medicament or fine particles comprising a medicament become adsorbed and adhered to the receptacle surfaces. It has been also found that when administering a medicament into the airway, even if the powder preparation contained in the receptacles is introduced into the airway by utilization of a gas pressurized by inhaled breath or some means, the fine particles adsorbed and adhered to the receptacle inner surfaces remain in the receptacles as such, so that the preparation does not reach the airway.

The above problem is quite insignificant, in the case of an oral preparation, which is to be administered together with the receptacles containing said preparation, even if the preparation is adsorbed and adhered to the inner surfaces of the receptacles, but in the case of a powder preparation for intratracheobronchial administration, in which the contents alone of the receptacles, not the receptacles themselves, are administered into the interior of the body, the amount of delivered content into the body is reduced, the problem becomes such a serious problem as may give an influence to the therapeutic effect of the preparation.

As a means of settling the present problem, there have hitherto been examined usually conceivable methods, such as a method of making fine particles, e.g. a method of enlarging the density of the powder preparation, a method of preliminarily adhering and adsorbing especially fine particles of the powder preparation to comparatively larger particles in the powder preparation, and the like, and it has been made clear that some methods are effective and the present problem has been settled e.g. in the case of corticosteroid preparation for intranaso-oral spraying administration. However, even if any of the above-mentioned methods is employed, depending upon the kind of a medicament, e.g. in peptides and proteins which exhibit noticeable absorptivity and adhesion properties to gelatin or plastics, there cannot be avoided adhesion and adsorption thereof to receptacles. In addition, when the powder preparation is kept under dried conditions especially for improvement of the physicochemical stability, it is very difficult, according to the above method, to prevent the powder preparation from being adhered and adsorbed to the receptacles.

Therefore, there have been demanded preparations for intratracheobronchial administration, which do not require troublesome formation of fine particles, which may be applied to various medicaments, and which are not adsorbed or adhered to the internal surfaces of the receptacles. There have been demanded also preparations for intratracheobronchial administration, which are not adsorbed or adhered to the inner surfaces of the receptacles, even under dried conditions.

Incidentally, the technical concept of employing hydroxypropyl methyl cellulose or the like as the material of receptacles for a medicament is already known. For example, Japanese Unexamined Patent Publication No. 61-100519 discloses medical hard capsules composed essentially of hydroxypropyl methyl cellulose.

On the other hand, it has already been known that various kinds of unit dose type receptacles and various multidose type receptacles, including medical hard capsules, have been used as receptacles for powder preparations for intratracheobronchial administration.

However, until now, it has not been a fact at all that in a powder preparation for intratracheobronchial administration, there may occur significant adhesion and/or adsorption of fine particles comprising a main medicament. It will be understood that to the present inventor's knowledge, the fact that the above adhesion adsorption phenomenon can be avoided by use of receptacles composed of hydroxypropyl methyl cellulose or the like, is novel and cannot be anticipated at all from the hitherto known literature or the like.

DISCLOSURE OF INVENTION

The purpose of the present invention is to provide a preparation for intratracheobronchial administration, which prevents the fine particles containing medicament from being adhered or adsorbed to the inner surfaces of the receptacles, so that the amount of the medicament delivered into the airway is improved.

More specifically, the purpose of the present invention is to provide a preparation for intratracheobronchial administration, which does not reduce the amount of the preparation delivered from receptacles to the airway, even if the preparation is stored under dry conditions.

In accordance with the present invention, there is provided a preparation for intratracheobronchial administration, which is contained in receptacles composed of at least one component selected from the group consisting of hydroxypropyl methyl cellulose, methyl cellulose, hydroxypropyl cellulose, starches, hydroxypropyl starches, and sodium alginate.

The present inventors have repeated their studies for settling the aforesaid problem, and found the astonishing fact that when a powder preparation for intratracheobronchial administration is contained in receptacles composed essentially of a cellulose derivative or analogue, i.e. a receptacle composed of at least one component selected from the group consisting of hydroxypropyl methyl cellulose, methyl cellulose, hydroxypropyl cellulose, starches, hydroxypropyl starches, and sodium alginate, the above-mentioned problem can be settled, and finally reached the present invention.

The adhesion/adsorption to the inner surface of receptacles of the medicament particles, or the particles comprising medicaments, contained in a receptacle is related to various factors including, for example, (1) the physical properties of the receptacle, (2) the physical properties of the medicament, (3) the physical properties of the particles of the additives copresent with the medicament particles and the particles comprising the medicament and (4) the environmental factors such as humidity is complicated.

It is clearly found as a result of our study heretofore that, when the medicament particles or particles comprising medicaments only are finely divided to a particle size necessary for the preparation for intratracheobronchial administration, i.e., about 500 μm or less irrespective of the presence of conventional additives, it is unavoidable irrespective of the physical properties and kinds of the medicament that the particles are adhered and adsorbed to conventional receptacles such as gelatin capsules, aluminum disks, polyethylene receptacles, but are not adhered and adsorbed to the receptacles according to the present invention. It is not clear why, to receptacles mainly composed of cellulose derivatives and analogues such as hydroxypropyl methyl cellulose, methyl cellulose, hydroxypropyl cellulose, starch, hydroxypropyl starch, sodium alginate, the above-mentioned particles are not adhered and adsorbed, due to the facts that the factors are complicated as mentioned above and the analysis thereof is difficult. However, these cellulose derivatives and analogues are not statically charged when contacted with the medicament particles or additive particles, but it is confirmed by our experiments that the statical charge occurs in the case of gelatin, polyethylene conventionally used as the receptacles.

BEST MODE FOR CARRYING OUT THE INVENTION

With respect to the shape of the receptacles used in the present invention, composed of hydroxypropyl methyl cellulose or the like, there may be adopted either a type, in which the preparation is preliminarily divided into each dose to be delivered into the airway for one time and each dose of the preparation is contained in each receptacle (unit dose type), or a type, in which the powder preparations for a plurality of doses are contained in a lump in a receptacle, such that a dose of powder preparation is divided from the receptacle and delivered into the airway by some means, every time the powder preparation is to be used (multidose type). In the case of a unit dose type, the receptacles may assume the shape of medical hard capsules, or the shape such that a unit dose is divided into some pieces and these pieces are contained in a receptacle on some places of the disk surface of the receptacle molded into a disk-shaped product. In addition, the receptacle may be molded into a proper shape in conformity with the shape of an administering utensil, and also may be a disposable receptacle integrated with an administering utensil. As a multidose type receptacle, any suffices if it is adequately molded in conformity with a multidose type administering utensil and has such a shape as has a function necessary to be charged in the multidose type administering utensil, when used, and put to practical use.

Although the proportion of hydroxypropyl methyl cellulose or the like based on the weight of a receptacle composed of the hydroxypropyl methyl cellulose or the like is limited by the hereafter-mentioned production process for the receptacle, it is preferably 70% by weight or more, and more preferably 80% by weight or more when a receptacle is composed of two or more kinds of components, the total weight of these components is desirably within the above range.

As the compounds to be compounded in a receptacle used in the present invention, composed of hydroxypropyl methyl cellulose or the like, there are mentioned plasticizers, thickening agents, auxiliary agents thereof, coloring matters, and the like. Specifical examples of these compounds are e.g. polyvinyl alcohol, polyethylene glycol, sorbitol, mannitol, sucrose, carrageenan, sodium chloride, potassium chloride, titanium oxide, lake coloring matter, and the like.

The receptacle is produced by use of at least one compound selected from the group consisting of hydroxypropyl methyl cellulose, methyl cellulose, hydroxypropyl cellulose, starch, hydroxypropyl starch, and sodium alginate. Of these compounds, hydroxypropyl methyl cellulose is favorable. As hydroxypropyl methyl cellulose to be used, with respect to the substitution ratio of the cellulose ether thereof, there is preferred one having a methoxyl group weight ratio ranging from 15 to 30% and a hydroxypropoxyl group weight ratio ranging from 3 to 15%, and with respect to the viscosity of the cellulose ether thereof, there is furthermore desired one having a viscosity of a 2% aqueous solution at 20° C., ranging from 2 to 20 cps. In addition, of usable hydroxypropyl methyl celluloses, with respect to the substitution ratio of the cellulose ether thereof, there are furthermore preferred hydroxypropyl methyl celluloses having a methoxyl group weight ratio ranging from 19 to 30% and a hydroxypropoxyl group weight ratio ranging from 4 to 12%. Further, as the hydroxypropyl methyl cellulose to be used, with respect to its viscosity, more desirable ones are hydroxymethyl celluloses having a viscosity of a 2% aqueous solution at 20° C., ranging from 3 to 15 cps.

The receptacle used in the present invention, composed essentially of hydroxypropyl cellulose, can be prepared in the same manner as a method for the preparation of hard gelatin capsules which have often been used as medical capsules. With respect to the details of the production processes of the capsules, there are disclosed in, e.g. Japanese Unexamined Patent Publication No. 61-100519, Japanese Unexamined Patent Publication No. 62-266060, Japanese Unexamined Patent Publication No. 63-127757, and Japanese Unexamined Patent Publication No. 3-9755. It will be easily understood that by these processes, there can be molded all the kinds of unit dose-type and multidose-type receptacles usable for powder preparations for intratracheobronchial administration, including medical capsules.

The powder preparation for intratracheobronchial administration, used in the present invention, comprises a medicament alone, revealing a pharmacological effect, or the medicament revealing the pharmacological effect and additives.

Of the medicaments revealing pharmacological effects, as a medicament revealing a pharmacological effect at an affected part in the airway, there are mentioned e.g. steroidal antiinflammatory drugs such as hydrocortisone, prednisone, prednisolone, triamcinolone, triamcinolone acetonide, dexametlon, betamethasone, beclometasone, and beclometasone dipropionate; non-steroidal antiinflammatory drugs such as acetoaminophenone, phenacetin, aspirin, aminopyrin, sulpyrine, phenylbutazone, mefenamic acid, ibufenac, ibuprofen, alclofenac, dichlofenac sodium, indomethacin, colchicine, and probenecid; enzymatic antiinflammatory drugs such as chymotrypsin, promelaincerapetase; antihistamines such as diphenhydramine hydrochloride, chloropheniramine maleate, and clemastine; antiallergic agents (antitussive, expectorant and antastimatic drugs) such as disodium cromoglycate, codeine phosphate, and isoproterenol hydrochloride; antibiotics such as tetracycline hydrochloride, leucomycin, fradiomycin, penicillin, and the derivatives thereof, and erythromycin; chemotherapeutants such as sulfathiazole, and nitrofurazone; local anesthetics such as benzocaine; vasoconstrictors such as phenylephrine hydrochloride, tetrahydrozoline hydrochloride, naphazoline nitrate, oxymethazoline hydrochloride, and tramazoline hydrochloride; cardiac stimulants such as digitalis, and digoxin; vasolators such as nitroglycerine and papaverine hydrochloride; antimicrobial agents such as chlorophexidine hydrochloride, hexyl resorcin, decalinium hydrochloride, and ethacrydine; enzymes such as lysothium chloride, and dextranase; anticancer drugs such as furfonracil; erasrase inhibitors; sympathomimetic drugs such as salbutamol sulfate, procaterol hydrochloride, and orciprenaline, and phenoterol hydrobromide; parasympatholytic drugs (cholinergic blocking agents) such as ipratropium, and furtropium oxalate; sputum-solubilizing drugs such as acetyl cysteine sodium, and bromhexine; mucous-lubricating agents such as ambroxol; and the like.

In addition, of the medicaments revealing pharmacological effects, as the medicaments which are absorbed in the body fluid such as blood from the airway and reveal pharmacological effects to the whole body, there are mentioned peptides, proteins, i.e. polypeptides, having various physiological activities. Of the polypeptides, those having a molecular weight ranging from 300 to 300,000 are preferable, because these polypeptides are easily absorbed through the tracheobroncheal mucosa. The molecular weight of the polypeptides is especially preferably within the range between 1,000 and 150,000. As specifical examples of polypeptides having physiological activities, there are mentioned the following: e.g. peptide hormones such as insulin, angiotensin, vasopressin, desmopressin, felypressin, protylylene, luteinizing hormone, corticotropin, prolactin, somatropin, thyrotropin, luteinizing hormone, calcitonin, kallikrein, parathylin, glucagon, oxitocin, gastrin, secretin, serum gonadotropin, growth hormone, erythropoietin, angiotensin, urogastrone, renin, lypomodulin, calmodulin, and hANP (human Atrial Naturetic Polypeptide), the chemically modified compounds thereof or components thereof; biologically active proteins such as interferon, interleukin, transferrin, histaglobulin, macrocortin, and serum coagulator VIII; enzyme proteins such as lysozyme, and urokinase.

In addition, of the medicaments revealing pharmacological effects, as vaccines utilizing the antigen recognition function of the lymph organization in the airway, there may be mentioned pertussis vaccine, diphtheric vaccine, tetanus vaccine, influenza vaccine or lymphocyte increasing factor, fibrous leukocyte agglutinizing elements, and the like.

Among the medicaments used in the present invention, revealing the above-mentioned pharmacological effects, it is preferable to use the medicaments such that the physical loss due to the adhesion and adsorption thereof to the inner surface of the receptacles is the substantial loss of the administration amount, namely a small administration amount of a highly active medicament. The amount of the adhesion and adsorption to the inner surface of the receptacle largely depends upon 10 the contact area between the preparation and the inner surface of the receptacle. For example, when beclometasone dipropionate powder having a particle size of 5–10 μm is contained in a #2 gelatin capsule, the amount of adhesion and adsorption is about 10 μg. It should be, however, noted that the loss of the medicament due to the adhesion and adsorption is varied depending upon the shapes of the receptacles and the size of the receptacles based upon a unit dose or a multidose. Nevertheless, based upon the above-mentioned example of the beclometasone dipropionate, if it is assumed that the maximum amount of about 100 μg is lost for each dose, the administration amount, in which the above-mentioned amount of loss is substantial loss in the administration amount, is about 2 mg per one dose at maximum. Accordingly, it is not limited, but the use of the medicaments having a unit dose in one administration of about 2 mg or less is preferable. More specifically, the favorable ones are steroidal antiinflammatory drugs, sympathomimetic drugs, parasympatholytic drugs, peptides, proteins and vaccines.

Furthermore, the adhesion and adsorption to the receptacle are especially remarkable in the dried state, and therefore, the present invention is especially preferable in the case of medicaments which are dried for the stabilization. Examples of such medicaments are peptides, proteins, vaccines.

As the additives used together with the medicaments revealing pharmacological effects in the powder preparation for intratracheobronchial administration, used in the present invention, there may be used the additives which have hitherto been used in powder preparations for intratracheobronchial administration, or any additive may be used, as long as it is usable. As such additives, pharmaceutical vehicles are used, and as concrete examples thereof, there may be mentioned one or a plurality of members selected from cellulose ethers, water absorbent and slightly water soluble base materials, sugars, amino acids and the like.

Cellulose ethers are cellulose derivatives in which a plurality of hydroxyl groups of cellulose are at least partially etherified, and examples thereof include e.g. lower alkyl ethers of celluloses, lower hydroxyalkyl ethers, lower carboxyalkyl ethers, and the like. The ether groups are not necessarily limited to same kinds, and e.g. cellulose ethers having 2 or more kinds of ether groups, e.g. a lower alkyl group and a lower hydroxyl alkyl group in a molecule are included in the cellulose ethers of the above category. Of these cellulose ethers, lower alkyl ethers of celluloses or lower hydroxyalkyl ethers are favorably used. The term, "lower alkyl" herein referred to means an alkyl group with 5 or less carbon atoms, preferably 3 or less carbon atoms.

As the above-mentioned cellulose ethers, there may be mentioned methyl cellulose, ethyl cellulose, hydroxyethyl cellulose, hydroxypropyl cellulose, carboxymethyl cellulose, carboxyethyl cellulose, carboxymethylhydroxy cellulose, hydroxypropyl methyl cellulose, and the like. Among them, there is preferably used especially methyl cellulose, hydroxyethyl cellulose, hydroxypropyl cellulose or hydroxypropyl methyl cellulose.

As the cellulose ethers, e.g. those having a viscosity of the 2% by weight aqueous solution thereof at 20° C., ranging from 3 to 100,000 centipoises, more preferably from 3 to 10,000 centipoises, especially preferably from 6 to 6,000 centipoises are preferably used.

As the cellulose ethers, e.g. those having an ether substitution degree ranging from 0.1 to 6.0, especially from 0.4 to 4.6 are preferably used. The term, "ether substitution degree", herein referred to means the average number of ether groups per glucose unit composing the cellulose, with regard to three hydroxyl groups of said one unit.

As the water absorbable and slightly water soluble bases, there may be mentioned e.g. water absorbable and slightly water soluble celluloses such as crystalline cellulose, α-cellulose, and cross-linked carboxymethyl cellulose sodium; water absorbable and slightly water soluble starches such as hydroxypropyl starch, carboxymethyl starch, cross-linked starch, amylose, amylopectin, and pectin; water absorbable and slightly water soluble proteins such as gelatin, casein, and casein sodium; water absorbable and slightly water soluble gums such as gum Arabic, gum tragacanth, and glucomannan; cross-linked vinyl polymers such as polyvinyl polypyrrolidone, cross-linked polyacrylic acid and the salts thereof, cross-linked polyvinyl alcohol, and polyhydroxymethyl methacrylate. Of these bases, water absorbable and slightly water soluble celluloses are preferable, and especially crystalline cellulose is favorable.

As the sugars, there may be mentioned glucose, annitol, lactose, fructose, dextran, and the like.

As the amino acids, there may be mentioned glycine, alanine and the like. In addition, besides these pharmaceutical vehicles, there are added, if necessary, a dispersion auxiliary agent, lubricant, stabilizer, and the like.

Now, the above-mentioned additives and the medicaments exhibiting the pharmacological effects may be present in the separate particles in the preparations or may form the same particles together. In the former case, the additives and the medicaments can be mixed, for example, mechanically. In the latter case, the additives and the medicament may be dispersed or dissolved in a solvent or solvents, followed by, for example, spray drying to form the preparation.

Now, the preparation for intratracheobronchial administration from the above-mentioned receptacle and powder preparation (comprising a medicament alone or the medicament and additives) is described. The production process thereof varies according to the aimed region in the airway, to which the medicament is to be delivered. That is, as described above, it is said that the region in the airway, to which a medicament can be delivered, is determined in accordance with the particle diameter of a preparation; e.g. particles with a particle diameter of more than about 10 μm, but not more than about 500 μm are deposited mainly in the oral cavity and nasal cavity, those having a particle diameter more than 2 μm but not more than 10 μm are deposited mainly in the trachea, bronchi, and bronchiole, and those having a particle diameter ranging from 0.5 to 2 μm are deposited mainly in the alveoli. Therefore, by adjusting the particle diameter of the powder preparation, it is possible to efficiently deliver the medicament to the targeted region. Perferably, at least 80 percent by weight of the particles in the powder preparation will have a diameter ranging from about 0.5 to 149 μm.

First, in order to deliver the medicament in the oral cavity and nasal cavity, it suffices, if the particle diameter of the powder preparation to be contained in the receptacles of the present invention is adjusted to a value greater than 10 μm, but not more than 500 μm. Among such powder preparations, as an example of preparation for topical application, there may be mentioned e.g. a curative medicine for nasal allergy, which is obtained by mixing e.g. beclometasone dipropionate, a steroidal antiinflammatory drug, having a particle diameter of more than 10 μm, but not more than 500 μm and hydroxypropyl cellulose, an additive having a particle diameter of more than 10 μm, but not more than 500 μm by a mixer. In the above case, in order to maintain the effect of the medicament for a long time, as the additives to be compounded into the preparation together with the main ingredient of the preparation, cellulose esters such as the exemplified hydroxypropyl cellulose are preferable. As other drugs for local application, there may be mentioned the other steroidal antiinflammatory drugs, non-steroidal antiinflammatory drugs, enzymatic antiphlogistics, antihistamic agents, antiallergic agents, vasoconstrictors, and the like. In addition, among the same kinds of powder preparations as above, as medicines for whole body, there are mentioned, e.g. transnasal preparations, the main medicament of which is proceeded to the vascular flow through the nasal mucosa and exhibits systemic action, and these transnasal preparations are prepared by mixing e.g. calcitonin with a particle size larger than 10 μm, but not more than 500 μm, e.g. salmon calcitonin with microcrystalline cellulose with a particle size larger than 10 μm, but not more than 500 μm by a mixer. In the above case, in order to obtain rapid onset of medical effect and good absorption, as the additives to be compounded into the preparation together with the main medicament, there are preferred the water absorbent and slightly water soluble bases as exemplified above. As the other medicaments for whole body, there may be mentioned peptides other than calcitonin, polypeptides such as proteins, vaccines, and the like.

Next, in order to deliver the medicament into the trachea, bronchi, bronchioles, and alveoli, it suffices, if the particle diameter of the powder preparation to be contained in the receptacles of the present invention is adjusted within the range between 10 μm and 0.5 μm. In the above case, all the particles do not necessarily need to have a particle diameter within the above range, but the more of whole amount of the particles having a particle diameter within the above range, the more the amount of the particles delivered into the trachea, bronchi, bronchioles, and alveoli.

Of these powder preparations, as medicament for local effect, there may be mentioned e.g. an antiasthmatic agent, which is prepared by making e.g. beclometasone dipropionate, a steroidal antiinflammatory drugs, and hydroxypropyl cellulose, an additive, and spray drying the mixture as fine particles having a particle diameter ranging from 10 to 0.5 μm. As other medicaments for local action, there may be mentioned the other steroidal antiinflammatory drugs, non-steroidal antiinflammatory drugs, enzymatic antiinflammatory drugs, antiallergic agents, antihistamic agents, elastase inhibitors, sympathomimetic drugs, parasympatholytic drugs, keratolytic drugs, mucosa swelling agents, and the like.

In addition, of the same kinds of preparations as above, as medicament for systemic effect, there may be mentioned a transpulmonary preparation, the main medicament of which proceeds into the vascular flow through the alveolo mucosas and exhibits systemic effect, which is obtained by making e.g. insulin and dextrose into fine particles having a particle diameter ranging from 10 to 0.5 μm. As other medicaments for whole body effect, there may be mentioned other peptides, polypeptides such as proteins, and the like. As the additives used in these powder preparations to be delivered into the trachea, bronchi, bronchioles, and alveoli, slightly stimulative and water soluble ones are desirable, and e.g. sugars, amino acids, and water soluble cellulose ethers are preferable.

The preparation of the present invention is administered into the respiratory tract through the nasal cavity or oral cavity, and the power source necessary for the preparation of the present invention, contained in the receptacles, to be introduced into the airway through the nasal and oral cavities, may be either the breathed air (inhalation) of a patient himself or a power source other than the breathed air of the patient, e.g. a balloon method or the like.

The powder preparation for intratracheobronchial administration, used in the present invention, is contained in the aforesaid receptacles used in the present invention, composed of the components such as hydroxypropyl methyl cellulose or the like, and thereby obtained in the form of a preparation. The shape of the receptacles is selected in conformity with the structure of the administering utensil, and therefore, the structure of the administering utensil is significant.

The structure of the administering utensil used when administering the powder preparation of the present invention is subjected to no restriction, as a general rule, and any administering utensil may be used, as long as it is the administering utensil (administering device) which has hitherto been used or proposed. As a unit dose type administering utensil, there may be mentioned e.g. the powder preparation-administering device (Japanese Examined Patent Publication No. 63-6024) corresponding to the medical hard capsule, "Spinhaler" (Registered Trade Mark), "Rotahaler" (Registered Trade Mark), "Diskhaler" (Registered Trade Mark) and the like.

In addition, as administering utensil corresponding to the multidose type receptacles, there may be mentioned e.g. "Turbohaler" (Registered Trade Mark), and the like.

Industrial Applicability

As explained above, according to the present invention, when a preparation for intratracheobronchial administration comprising a powder preparation for intratracheobronchial administration contained in receptacles composed of hydroxypropyl methyl cellulose or the like is administered into the airway by such an administering utensil as described above, the powder preparation is adhered or adsorbed to the receptacle inner surfaces in a less amount than the case where a powder preparation contained in conventional receptacles is administered into the airway by such an administering utensil as above, so that the amount of the present powder preparation actually delivered into the airway is larger, which fact is very meaningful in view of the curative effect.

EXAMPLES

The present invention will now be further explained in detail with reference to the Examples, but it is to be noted that the present invention is not limited thereto.

Examples 1 to 16, Control Examples 1 to 64

The following experiments were performed for the purpose of clarifying that a powder preparation for intratracheobronchial administration exhibits only slight adhesiveness/adsorptiveness to receptacles composed essentially of hydroxypropyl methyl cellulose.

(1) Production of a measuring box for the amount of the powder preparation adhered/adsorbed to various receptacle materials:

A box having one square base with a side length of 2 cm and a height of 1 cm, the other base being opened, was made of a cardboard, and a thin filmy material described in the following item (2) was stuck to the 5 faces confronting the inside of the box (4 lateral faces and one base) with "Alon alpha" (produced by Toa Gosei Kagaku).

(2) Preparation of the thin filmy material to be stuck to the inner faces of the measuring box for adhered/adsorbed amount:

As described in the following, there were prepared five kinds of materials including the material composed essentially of hydroxypropyl methyl cellulose.

Material A: A thin film with a thickness of 0.1 mm, consisting of 93 parts by weight of hydroxypropyl methyl cellulose (produced by Shinetsu Kagaku, trade name: "TC-5R": methoxyl group: 28 to 30% by weight, hydroxypropoxyl group: 7 to 12% by weight, viscosity of a 2% aqueous solution at 20° C.: 6 cps), 1 part by weight of carrageenan (produced by Wako Junyaku), 1 part by weight of potassium chloride (produced by Wako Junyaku), and 5 parts by weight of water. (A solution obtained by dissolving above substances in an excessive amount of water was spread on a flat plate, and dried so as to be formed into a uniform filmy product.)

Material B: A thin film with a thickness of 0.1 mm, consisting of 95 parts by weight of gelatin (produced by Wako Junyaku) and 5 parts by weight of water. (A solution obtained by dissolving the gelatin in an excessive amount of water was spread on a flat plate, and dried so as to be formed into a uniform filmy product.)

Material C: Polypropylene sheet (A sheet produced by Nikko was used as such.)

Material D: Aluminium foil (A Nippaku foil was used as such.)

Material E: Ordinary thin sheet glass.

(3) Preparation of a powder preparation for intratracheobronchial administration, comprising a medicament:

The medicaments, bases, and lubricants described in Table 1 were mix-prepared by the methods described in Table 1, respectively, so that powder preparations for intratracheobronchial administration were prepared. The particle size distributions of the prepared powder preparations are also set forth in Table 1.

(4) Method of determining the amount of the adhered and adsorbed medicament:

Each 100 mg of the powder preparations for intratracheobronchial administration, prepared in the above (3) were introduced into the measuring boxes described in (1), which had been lined, respectively, with the materials described in (2), and each of the boxes was shaked right and left by a shaker, so that each powder preparation was brought into contact with each material. During the shaking operation, the top open face was covered in order to prevent the content of the box from being scattered. (These experiments were performed under the conditions of 25° C./40% RH.) After the shaking operation had been completed, the lid was removed and the contents were taken out. The powder preparations were, respectively, discharged by tapping the box with a spatula, or by other means, until the powder preparation could not be recognized with naked eyes on the base and lateral faces of the box. The discharged powder preparations were collected and the medicament contained therein was measured by high speed liquid chromatography, whereupon the amount of powder preparation adhered or adsorbed in the inner faces of the box was calculated on the basis of the amount of the powder preparation initially introduced in the box. The results of Examples 1 to 16, with variation of the combinations of the receptacle materials and powder preparations, are set forth in Table 2, and the results of Contrast Examples 1 to 64, with variation of the combinations of the conventional receptacle materials and powder preparations are set forth in Table 3.

TABLE 1

| Powder Prep. No. | Medicament | Base | Lubricant | Preparation method | Remarks |
|---|---|---|---|---|---|
| 1 | Salmon calcitonin[1] (100 I.U.) | Microcrystalline cellulose[10] | Magnesium stearate[15] | a | Preparation for nasal cavity |
| 2 | Salmon calcitonin[1] (100 I.U.) | Cross-linked starch[11] | Magnesium stearate[15] | a | Preparation for nasal cavity |
| 3 | Insulin[2] (5 I.U.) | Microcrystalline cellulose | Magnesium stearate[15] | a | Preparation for nasal cavity |
| 4 | Insulin[2] (5 I.U.) | Hydroxypropyl cellulose[12] | Magnesium stearate[15] | b | Inhalant |
| 5 | Insulin[2] (5 I.U.) | Hydroxypropyl cellulose[12] | Magnesium stearate[15] | c | Inhalant |
| 6 | LHRH[3] (400 μg) | Microcrystalline cellulose | Magnesium stearate[15] | a | Preparation for nasal cavity |
| 7 | LHRH[3] (400 μg) | Lactose[13] | Magnesium stearate[15] | b | Inhalant |
| 8 | LHRH[3] (400 μg) | Hydroxypropyl cellulose | Magnesium stearate[15] | c | Inhalant |
| 9 | Beclometasone dipropionate[4] (400 μg) | Hydroxypropyl cellulose | Magnesium stearate[15] | a | Preparation for nasal cavity |
| 10 | Beclometasone dipropionate[4] (400 μg) | Lactose | Magnesium stearate[15] | b | Inhalant |
| 11 | Beclometasone dipropionate[4] (400 μg) | Hydroxypropyl cellulose | Magnesium stearate[15] | c | Inhalant |
| 12 | Salbutamol sulfate[5] (100 μg) | Hydroxypropyl cellulose | Magnesium stearate[15] | b | Inhalant |
| 13 | Ipratropium bromide[6] (40 μg) | Hydroxypropyl cellulose | Magnesium stearate[15] | c | Inhalant |
| 14 | Triamcinolone | Hydroxypropyl | Magnesium | a | Preparation |

TABLE 1-continued

| Powder Prep. No. | Medicament | Base | Lubricant | Preparation method | Remarks |
|---|---|---|---|---|---|
| | acetonide[7] (400 μg) | methyl cellulose[14] | stearate[15] | | for nasal cavity |
| 15 | Procaterol hydrochloride[8] (50 μg) | Hydroxypropyl methyl cellulose[14] | Magnesium stearate[15] | b | Inhalant |
| 16 | Fenoterol hydrobromide[9] (200 μg) | Hydroxypropyl cellulose | Magnesium stearate[15] | c | Inhalant |

[1] produced by Sigma Inc.
[2] produced by Sigma Inc.
[3] produced by Peptide Research Institute
[4] produced by Sigma Inc.
[5] produced by Sigma Inc.
[6] produced by Sigma Inc.
[7] produced by Sigma Inc.
[8] produced by Sigma Inc.
[9] produced by Sigma Inc.
[10] "Apicel PH101" produced by Asahi Kasei
[11] produced by Nichiden Kagaku
[12] "HPC-H" produced by Nippon Soda Inc.
[13] produced by Megle
[14] "TC-5R" produced by Shinetsu Kagaku In Table 1, the content in 30 mg of each powder preparation was shown in each pair of parentheses. In addition, the content of magnesium stearate was 0.5% by weight of each powder preparation. Mix-preparation was effected in the following manner.

a) To a predetermined amount of the medicament having a particle diameter of 46–149 μm, there was added a base having 90% by weight or more of particles with a particle diameter ranging from 46–149 μm, followed by mixing in a small-sized V-type mixer until the mixture becomes uniform and finally 0.5% of magnesium stearate was mixed to the obtained mixture, whereby a homogeneous powder preparation for intranasal administration was obtained.

b) To a predetermined amount of the medicament having a particle diameter of 0.5–10 μm, there was added a base having 90% or more of particles with a particle diameter of 46–149 μm, followed by mixing in a small-sized v-type mixer until the mixture becomes uniform, and finally 0.5% of magnesium stearate was mixed to the obtained mixture, whereby a homogeneous powder preparation for internasal administration was obtained.

c) A predetermined amount of a medicament and base were dissolved into a solvent composed essentially of water (ethanol was added, if necessary), and the obtained solution was spray dried to prepare a powder of minute particles, whereafter 0.5% of magnesium stearate was added to the obtained powder, so that a powder preparation (inhalant) for intratracheobronchial administration was obtained.

The particle size distribution of the powder preparations obtained by the above-mentioned preparing method c) was 0.5 to 10 μm for 80% or more thereof. The results obtained by use of a laser type particle size measuring machine (JEOL/SYMPATEC; HEROS & ROODS).

TABLE 2

| Example | Receptacle Material | Powder Preparation | Adhering/Adsorbing Rate (%) |
|---|---|---|---|
| 1 | A | 1 | 2 |
| 2 | A | 2 | 3 |
| 3 | A | 3 | 3 |
| 4 | A | 4 | 7 |
| 5 | A | 5 | 8 |
| 6 | A | 6 | 4 |
| 7 | A | 7 | 6 |
| 8 | A | 8 | 7 |
| 9 | A | 9 | 2 |
| 10 | A | 10 | 4 |
| 11 | A | 11 | 7 |
| 12 | A | 12 | 2 |
| 13 | A | 13 | 3 |
| 14 | A | 14 | 3 |
| 15 | A | 15 | 4 |
| 16 | A | 16 | 5 |

TABLE 3

| Example | Receptacle Material | Powder Preparation | Adhering/Adsorbing Rate (%) |
|---|---|---|---|
| 1 | B | 1 | 15 |
| 2 | " | 2 | 18 |
| 3 | " | 3 | 20 |
| 4 | " | 4 | 23 |
| 5 | " | 5 | 26 |
| 6 | " | 6 | 17 |
| 7 | " | 7 | 19 |
| 8 | " | 8 | 25 |
| 9 | " | 9 | 19 |
| 10 | " | 10 | 18 |
| 11 | " | 11 | 27 |
| 12 | " | 12 | 20 |
| 13 | " | 13 | 16 |
| 14 | " | 14 | 19 |
| 15 | " | 15 | 20 |
| 16 | " | 16 | 24 |
| 17 | C | 1 | 31 |
| 18 | " | 2 | 28 |
| 19 | " | 3 | 34 |

TABLE 3-continued

| Example | Receptacle Material | Powder Preparation | Adhering/Adsorbing Rate (%) |
|---|---|---|---|
| 20 | " | 4 | 45 |
| 21 | " | 5 | 49 |
| 22 | " | 6 | 30 |
| 23 | " | 7 | 35 |
| 24 | " | 8 | 37 |
| 25 | " | 9 | 29 |
| 26 | " | 10 | 26 |
| 27 | " | 11 | 46 |
| 28 | " | 12 | 36 |
| 29 | " | 13 | 33 |
| 30 | " | 14 | 29 |
| 31 | " | 15 | 32 |
| 32 | " | 16 | 43 |
| 33 | D | 1 | 18 |
| 34 | " | 2 | 19 |
| 35 | " | 3 | 21 |
| 36 | " | 4 | 23 |
| 37 | " | 5 | 30 |
| 38 | " | 6 | 20 |
| 39 | " | 7 | 20 |
| 40 | " | 8 | 28 |
| 41 | " | 9 | 16 |
| 42 | " | 10 | 18 |
| 43 | " | 11 | 21 |
| 44 | " | 12 | 15 |
| 45 | " | 13 | 17 |
| 46 | " | 14 | 19 |
| 47 | " | 15 | 20 |
| 48 | " | 16 | 22 |
| 49 | E | 1 | 19 |
| 50 | " | 2 | 18 |
| 51 | " | 3 | 18 |
| 52 | " | 4 | 25 |
| 53 | " | 5 | 27 |
| 54 | " | 6 | 16 |
| 55 | " | 7 | 17 |
| 56 | " | 8 | 21 |
| 57 | " | 9 | 15 |
| 58 | " | 10 | 14 |
| 59 | " | 11 | 28 |
| 60 | " | 12 | 13 |
| 61 | " | 13 | 14 |
| 62 | " | 14 | 15 |
| 63 | " | 15 | 16 |
| 64 | " | 16 | 23 |

From Table 2 and Table 3, it can be seen that the adhesiveness/adsorptiveness of the powder preparation for intratracheobronchial administration to receptacles composed essentially of hydroxypropyl methyl cellulose is less than that to receptacles made of gelatin, polypropylene, aluminium foil or glass.

Examples 17–21, Control Examples 65–69

The powder preparations 1, 3, 6, 9 and 14 described in the above Table 1 were filled up into medical hard capsules composed essentially of hydroxypropyl methyl cellulose (composition: 93 parts by weight of hydroxypropyl methyl cellulose, "TC-5R" produced by Shinetsu Kagaku; 1 part by weight of carrageenan; 1 part by weight of potassium chloride; 5 parts by weight of water), in an amount of 30 mg, respectively, and, after storing at 25° C. and 55% RH for 2 weeks, the powder preparations were sprayed by a powder preparation-administering device (Japanese Examined Patent Publication No. 63-6024) until the powder preparation could not be recognized with naked eyes, following which the above-mentioned capsules were taken out and the medicament remained in the capsule inner faces was subjected to measurement by HPLC, whereby the adhesion-adsorption ratio of the powder preparation to the capsule inner faces was calculated. (Examples 17–21).

In addition, the powder preparations 1, 3, 6, 9, and 14 also described in the above Table 1 were, respectively, filled up into each of medical capsules composed essentially of gelatin (composition: 95 parts of gelatin and 5 parts by weight of water) in an amount of 30 mg, whereupon the same experiments as described in Examples 17 to 21 were conducted. (Control Examples 65–69).

The results are set forth in Table 4.

TABLE 4

| | Rate of Adhesion/Adsorption (%) | |
|---|---|---|
| | 25° C./55% RH | Drying Conditions |
| Example | | |
| 17 | 2 | 4 |
| 18 | 4 | 5 |
| 19 | 3 | 5 |
| 20 | 5 | 7 |
| 21 | 5 | 7 |
| Control Example | | |
| 65 | 9 | 25 |
| 66 | 13 | 43 |
| 67 | 10 | 39 |
| 68 | 19 | 47 |
| 69 | 25 | 46 |

It may be seen from Table 4 that the proportion of the powder preparation for intratracheobronchial administration remained in the insides of capsules, when the powder preparation filled in the capsules composed essentially of hydroxypropyl methyl cellulose is sprayed from a powder preparation-administering device, is less than the proportion of the preparation remained when the preparation is filled in gelatin capsules and simultaneously sprayed, and also that the amounts of the adhesion/adsorption are not affected by the drying. Note that there are some gelatin capsules causing cracks during drying.

Examples 22, 23, and Contrast Examples 70 and 71

The powder preparations 4 and 11 described in the above Table 1 were filled up in medical hard capsules composed essentially of hydroxypropyl methyl cellulose in an amount of 5 mg, respectively, like Examples 17 to 21, and holes were made in the capsules by use of a powder preparation-administering device in the same way as described in the above Examples 17 to 21, following which a suction pump was connected to the device and the contents of the capsules were sucked at a rate of 60 liter/min by this suction pump, whereafter the amount of main medicament remained on the capsule inner faces was determined by the similar way, so that the rate of the medicament adhered to the capsule inner faces was calculated (Examples 22 and 23).

The same experiments were performed also with respect to the same powder preparations 4 and 11 filled up in gelatin capsules, whereby the rates of the powder preparations adhered to the capsule inner faces were calculated, respectively. (Contrast Examples 70 and 71).

The results are set forth in Table 5.

TABLE 5

| | Rate of Adhesion/Adsorption |
|---|---|
| Example 22 | 5 |
| Example 23 | 4 |

TABLE 5-continued

| | Rate of Adhesion/Adsorption |
|---|---|
| Contrast Example 70 | 18 |
| Contrast Example 71 | 23 |

It can be seen from Table 5 that the proportion of the contents of a powder preparation for intratracheobronchial administration, remained in the insides of capsules, when the contents of the preparation filled up in capsules composed essentially of hydroxypropyl methyl cellulose are sucked in the same manner as human inhalation is less than the proportion of the preparation remained in gelatin capsules when the contents of the preparation filled up in the gelatin capsules are sucked in the same way as above.

Examples 24 to 28

Thin film-like materials, each composed of the following materials F, G, H, I, and J, respectively, were prepared, in the same way as in Examples 1 to 16.

Material F: A thin film with a thickness of 0.1 mm consisting of 95 parts by weight of methyl cellulose ("Metholose SM 15" produced by Shinetsu Kagaku) and 5 parts by weight of water (A solution obtained by dissolving the methyl cellulose with an excessive amount of cooled water was spread on a flat plate, whereafter it was dried so as to form a uniform thin film.)

Material G: A thin film with a thickness of 0.1 mm, consisting of 95 parts by weight of hydroxypropyl cellulose ("Nisso HPC-M") and 5 parts by weight of water (A solution obtained by dissolving the hydroxypropyl cellulose with an excessive amount of cooled water was spread on a flat plate, whereafter it was dried so as to be formed into a uniform thin film.)

Material H: A thin film with a thickness of 0.1 nun, consisting of 95 parts by weight of starch (Indian corn starch produced by Nippon Shokuhin Kako [Japan Food Processing Industries Co., Ltd.] and 5 parts by weight of water (The starch was solubilized with boiling water, whereafter the solubilized starch was spread on a flat plate, following which it was dried so as to form a uniform thin film.)

Material I: A thin film with a thickness of 0.1 mm, consisting of 95 parts by weight of hydroxypropyl starch ("HPS 101 (W)" produced by Freund Industries Inc.) and 5 parts by weight of water (The hydroxypropyl starch was solubilized with boiling water, whereafter the solubilized starch was spread on a flat plate, following which it was dried so as to form a uniform thin film.)

Material J: A thin film with a thickness of 0.1 mm, consisting of 95 parts by weight of sodium alginate (produced by Kimitsu Chemical Inc.) and 5 parts by weight of water (A solution obtained by dissolving the sodium alginate in cool water was spread on a flat plate, following which it was dried to form a uniform thin film.)

For these materials F to J, and the powder preparation 1 of Examples 1 to 16, the same experiments as in Examples 1 to 16 were performed, whereby the adhesion/adsorption rates of the powder preparation 1 to the materials F to J were determined, respectively. The results are set forth in Table 6.

TABLE 6

| Example | Receptacle Material | Powder Preparation | Adhesion/Adsorption Rate (%) |
|---|---|---|---|
| 24 | F | 1 | 4 |
| 25 | G | 1 | 2 |
| 26 | H | 1 | 3 |
| 27 | I | 1 | 3 |
| 28 | J | 1 | 3 |

It can be seen from Table 6 that the adhesion/adsorption rates of a powder preparation for intratracheobronchial administration, to the receptacles, composed essentially of methyl cellulose, hydroxypropyl cellulose, starch, hydroxypropyl starch, and sodium alginate, respectively, are low in the same degree as the adhesion/adsorption rates of the same preparation to a receptacle composed essentially of hydroxypropyl methyl cellulose.

We claim:

1. A preparation for intratracheobronchial administration comprising a powder preparation for intratracheobronchial administration contained in a receptacle comprising at least one component selected from the group consisting of hydroxypropyl methyl cellulose, methyl cellulose, hydroxypropyl cellulose, starch, hydroxypropyl starch, and sodium alignate, wherein the amount of said component is at least 80% by weight of said receptacle, and wherein at least 80% by weight of the particles in said powder preparation, based on the weight of said preparation, have a diameter ranging from about 0.5 to 149 μm.

2. A preparation for intratracheobronchial administration as claimed in claim 1, wherein said component is hydroxypropyl methyl cellulose.

3. A preparation for intratracheobronchial administration as claimed in claim 1, wherein said receptacle is molded so as to charged as a unit dose or a multidose in an administering utensil for intratracheobronchial administration of powder.

4. A preparation for intratracheobronchial administration as claimed in claim 3, wherein said receptacle is charged as a unit dose in the administering utensil for intratracheobronchial administration of powder, which is a medical hard capsule.

5. A preparation for intratracheobronchial administration as claimed in claim 1, wherein said receptacle is integrated with an administering utensil for intratracheobronchial administration of said powder, and is disposable.

6. A preparation for intratracheobronchial administration as claimed in any one of claims 1 or 2–5, wherein said powder preparation for intratracheobronchial administration is a powder preparation which is inhaled through a nasal cavity and deposited in the nasal cavity.

7. A preparation for intratracheobronchial administration as claimed in any one of claims 1 or 2–5, wherein said powder preparation for intratracheobronchial administration is a powder preparation which is sprayed into a nasal cavity and deposited in the nasal cavity.

8. A preparation for intratracheobronchial administration as claimed in any one of claims 1 or 2–5, wherein said powder preparation for intratracheobronchial administration is a powder preparation which is inhaled through an oral cavity and deposited in the oral cavity, pharynx, larynx, trachea, bronchi, bronchioles, or alveoli.

9. A preparation for intratracheobronchial administration as claimed in any one of claims 1 or 2–5, wherein said powder preparation for intratracheobronchial administration is a powder preparation which is sprayed into a oral cavity and deposited in the oral cavity, pharynx, larynx, trachea, bronchi, bronchioles, or alveoli.

10. A preparation for intratracheobronchial administration as claimed in any one of claims 1 or 2–5, wherein said powder preparation for intratracheobronchial administration is that comprising a medicament selected from the group consisting of antiallergic drugs, steroidal antiinflammatory drugs, non-steroidal antiinflammatory drugs, enzymatic antiinflammatory drugs, antihistamines, antibiotics, germicides, chemotherapeutic drugs, elastase inhibitors, local anesthetics, vasoconstrictors, cardiacs, vasodilators, anti-malignant-tumor drugs, sympathomimetic drugs, sympatholytic drugs, parasympatholytic drugs, sputum solubilizers, mucosa lubricants, peptides, proteins, and vaccines.

11. A preparation for intratracheobronchial administration as claimed in claim 10, wherein said powder preparation for intratracheobronchial administration further comprises a pharmaceutical vehicle to be administered simultaneously with said medicament, said pharmaceutical vehicle being selected from the group consisting of cellulose ethers; water absorbable and slightly water soluble celluloses, water absorbable and slightly water soluble proteins; water absorbable and slightly water soluble gums; water absorbable and slightly water soluble cross-linked vinyl polymers; sugars; and amino acids.

12. The preparation for intratracheobronchial administration as claimed in any one of claims 1 or 2–5, wherein said powder preparation for intratracheobronchial administration is that comprising a medicament selected from the group consisting of steroidal antiinflammatory drugs, sympathomimetic drugs, parasympatholytic drugs, peptides and proteins.

13. The powder preparation for intratracheobronchial administration as claimed in claim 12, wherein said powder preparation for intratracheobronchial administration further comprises a pharamaceutical vehicle to be administration simultaneously with said medicament, wherein said pharmaceutical vehicle is selected from the group consisting of water absorbable and slightly water soluble celluloses; water absorbable and slightly water soluble starches; water absorbable and slightly water soluble proteins; water absorbable and slightly water soluble gums; and water absorbable and slightly water soluble cross-linked vinyl polymers.

* * * * *